United States Patent [19]

Horman et al.

[11] Patent Number: 4,725,733

[45] Date of Patent: * Feb. 16, 1988

[54] APPARATUS AND METHOD FOR REMOTELY DETECTING THE PRESENCE OF CHEMICAL WARFARE NERVE AGENTS IN AN AIR-RELEASED THERMAL CLOUD

[75] Inventors: Roger Horman, Dahlgren; Joseph Overman, Stuart Herndon, both of Fredericksburg, all of Va.

[73] Assignee: The United States of America as represented by the Secretary of the Navy, Washington, D.C.

[*] Notice: The portion of the term of this patent subsequent to Dec. 14, 1999 has been disclaimed.

[21] Appl. No.: 514,739

[22] Filed: Jul. 18, 1983

[51] Int. Cl.[4] .............................................. G01J 1/00
[52] U.S. Cl. ................................... 250/339; 250/338
[58] Field of Search ................... 250/339, 361 C, 330, 250/351, 338 GA; 356/320, 435, 437, 438; 324/466; 89/1.11

[56] References Cited

U.S. PATENT DOCUMENTS

| | | | |
|---|---|---|---|
| 4,043,668 | 8/1977 | Goetz et al. | 250/339 |
| 4,363,967 | 12/1982 | Efkeman et al. | 250/339 |
| 4,390,785 | 6/1983 | Faulhaber et al. | 250/339 |

Primary Examiner—Stephen C. Buczinski
Assistant Examiner—Linda J. Wallace
Attorney, Agent, or Firm—Kenneth E. Walden; Frederick A. Wein

[57] ABSTRACT

An apparatus and method for remotely detecting the presence of chemical warfare nerve agents in a suspect thermal cloud. Infrared radiation emitted by a suspect thermal cloud is analyzed by means of a forward looking infrared thermal imager equipped with a spectral filter wheel having four passband filters; three of the spectral filter elements are spectrally optimized to respond to infrared radiation emissions characteristic of chemical warfare nerve agents. The variations in image contrasts of the thermograms generated by selectively filtering the infrared radiation emitted by the suspect thermal cloud are compared to determine the presence or absence of chemical warfare nerve agents in the suspect thermal cloud.

13 Claims, 8 Drawing Figures

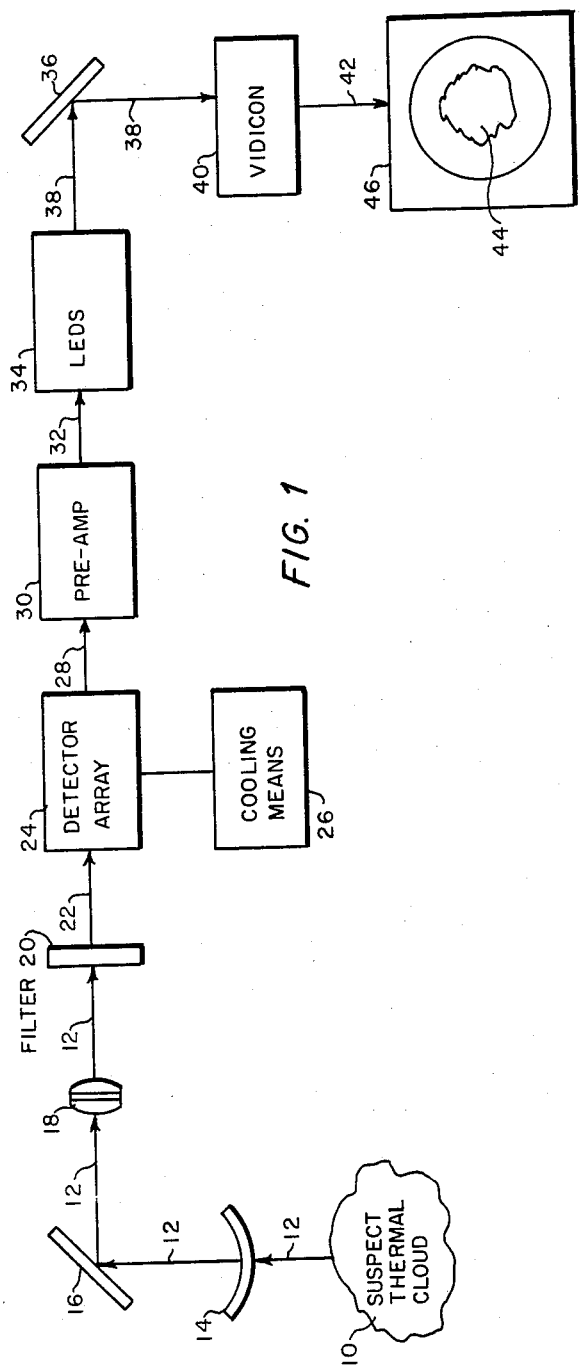
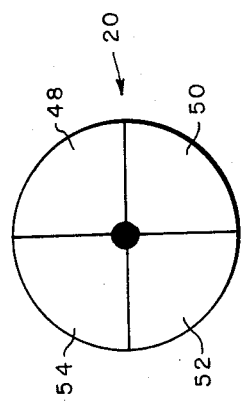

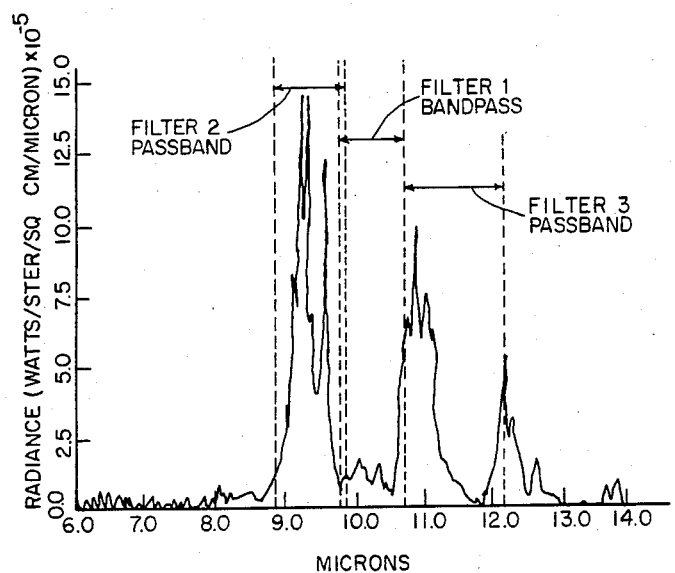
FIG. 3
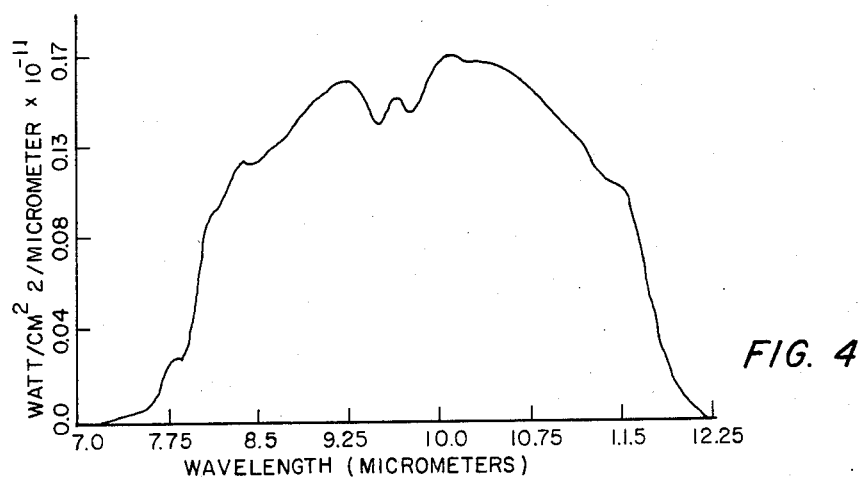
FIG. 4
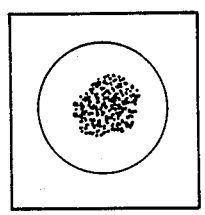 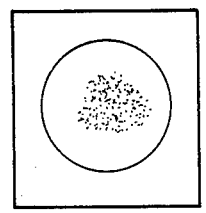 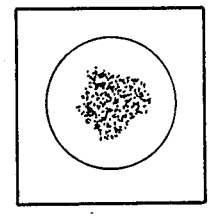 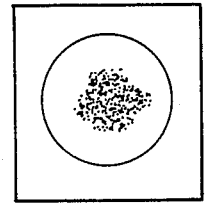
FIG. 5a    FIG. 5b    FIG. 5c    FIG. 5d

APPARATUS AND METHOD FOR REMOTELY DETECTING THE PRESENCE OF CHEMICAL WARFARE NERVE AGENTS IN AN AIR-RELEASED THERMAL CLOUD

BACKGROUND OF THE INVENTION

This invention relates generally to infrared radiation detection apparatus, and more particularly, to an apparatus and method for remotely detecting the presence of chemical warfare nerve agents in an air-released thermal cloud by analyzing its infrared radiation emission characteristics.

Certain potential enemies of the U.S. possess the capability to direct air-releases of a wide spectrum of lethal and incapacitating chemical warfare nerve agents against the U.S. Fleet. Air-releases of chemical warfare nerve agents, forming thermal clouds, may be effected by dispersal from aircraft or air-burst projectiles. These chemical warfare nerve agents are all organo-phosphorus compounds with strong, narrow infrared absorption bands near 9.8 and 10.75 microns. An interrogation of the infrared characteristics of an air-released thermal cloud must readily permit the detection of chemical warfare nerve agent constituents so that the Fleet may undertake effective countermeasures. The detection of chemical warfare nerve agents must be equally effective in a diurnal or nocturnal environment. The detection of chemical warfare nerve agent thermal clouds must be possible against the varied infrared backgrounds and naturally occuring infrared-emitting objects of the naval environment. The interrogation process must be sensitive enough to discriminate between chemical warfare nerve agent thermal clouds and interferent thermal clouds, i.e., those dispersants which mimic the visual characteristics of a chemical warfare nerve agent thermal cloud such as air-releases of JP-4 aviation fuel and the explosion products from the air-burst of high-explosive projectiles.

The prior art discloses gas analyzers which use infrared radiation to ascertain the chemical composition of a given gas sample; representative examples being U.S. Pat. Nos. 4,297,579 to T. Spaeth, 4,035,643 to J. Barrett, and 4,013,260 to McClatchie et al. These analyzers operate on the principle that a given gaseous element or compound will absorb infrared radiation at specific absorption bands characteristic of that element or compound. Typically, these devices use an active radiation source to generate infrared radiation which is then filtered so as to pass only infrared radiation in a specific absorption band, this absorption band being characteristic of one of the gaseous elements or compounds presumed to be a constituent of the gas sample. The filtered infrared radiation is then passed through a cell containing the gas sample and impinges upon an infrared radiation detection means. The detected infrared radiation is converted into an electrical output signal by means of electronic processing circuitry, the strength of the output signal being inversely proportional to the degree of absorption of the filtered infrared radiation passed through the gas sample. Variations in strength of the output signals at selected absorption bands may then be compared with reference signals generated by passing the same selected infrared radiation bands through the cell without the gas sample to determine the gaseous elements or compounds present in the gas sample. These gas analyzers are active, i.e., to operate they require an infrared radiation source as a component of the apparatus, and the gas sample to be analyzed must be contained within a cell in the apparatus. In contradistinction, a chemical warfare nerve agent detection apparatus, to be efficacious in a naval environment during a conflict scenario, must be a passive device, i.e., function based upon the infrared radiation emissivity characteristics of the chemical warfare nerve agents rather than their absorption characteristics, and must be capable of detecting chemical warfare nerve agents at remote distances.

U.S Pat. No. 2,930,893 to Carpenter et al discloses an apparatus and method for the remote detection of atmospheric contaminants, particularly highly toxic chemical warfare nerve agents. An infrared radiation source-receiver is encircled by a series of remotely positioned reflectors such that coded infrared radiation is transmitted through a detection area and then reflected back through the detection area to the receiver. An echelette grating in the receiver passes infrared radiation at selected infrared wavelengths; a detection band of mean wavelength of 9.8 microns at which the contaminant of interest exhibits strong absorption and reference bands at mean wavelengths of 9.25 and 10.4 microns to reduce the likelihood of any other contaminant in the detection area triggering a false alarm. The received infrared radiation is processed electronically so that a comparator circuit will generate an alarm whenever the toxic agent of interest is present in the detection area. This invention requires an active source of infrared radiation for the detection of chemical warfare nerve agents which detracts from its applicability in a mobile naval environment. Operationally this invention was designed for the detection of chemical warfare nerve agents over a fixed detection area inasmuch as the infrared radiation source-receiver must be encircled by fixed reflectors; this would reduce the invention's efficacy in a mobile naval environment. In addition, the invention's detection area is limited to the line-of-sight between the infrared radiation source-receiver and the fixed reflectors.

U.S. Pat. No. 3,848,129 to Figier et al is representative of passive radiation detection apparatus which is capable of discriminating between infrared radiation with different spectral characteristics. An optical device collects the incident infrared radiation which is then sequentially filtered by first and second bandpass spectral filters to pass infrared radiation of relatively long and short wavelengths. The filtered infrared radiation impinges upon a single detector to produce first and second sampling signals. The first and second sampling signals are compared to produce a comparison signal. A target signal is generated whenever the amplitude of the comparison signal is equal to or greater than a predetermined value. This type of infrared radiation detection apparatus is used to detect point sources of infrared radiation by processing infrared radiation emissions in two narrow spectral bands; the spectral bandpass for potential targets is in the 2.8 to 3.2 micron range while the spectral bandpass for point source background radiation is posited to be in the 2.0 to 2.5 micron range. Therefore this device functions on an either/or basis; intercepted infrared radiation emissions indicate either a true target or a false target. Chemical warfare nerve agents emit infrared radiation in two narrow spectral bands centered at 9.8 and 10.75 microns. In the naval environment, however, most naturally occuring objects have infrared radiation emission characteristics that change slowly with wavelength, i.e., their emissivity over the 8.0 to 14.0 micron atmospheric window is well approximated by that of a gray body; at any given time these objects, as well as interferents, could be emitting infrared radiation in the 9.8 and 10.75 spectral bands. Thus an either/or device would be incapable of discriminating between chemical warfare nerve agents and naturally occuring objects and/or interferents when their spectral characteristics are similar. Finally, an either/or device generates a target signal only when the intercepted infrared radiation generates a comparison signal that exceeds an internal reference; this presupposes a priori knowledge of the signal strength of a target. By comparison, the strength of the signal generated by chemical warfare nerve agents is dependant upon the apparent temperature difference between the chemical warfare nerve agent thermal cloud and its background, the agent concentration in the cloud, and the optical path through the agent cloud; these parameters vary with the physical, chemical and dispersal characteristics of chemical warfare nerve agents and the prevailing atmospheric conditions, and therefore, cannnot be postulated beforehand.

Infrared imaging devices, such as Texas Instruments Model AN/AAS-28, a forward looking infrared (FLIR) thermal-imagery sensor, convert an invisible infrared image into a two-dimensional video image, i.e., a thermogram. Infrared imaging devices are designed to operate within broad infrared wavelength regions of atmospheric transparency, the atmospheric windows. These atmospheric windows exist at approximately 8 to 14 microns, 3 to 5 microns, 2 to 2.5 microns, 1.5 to 1.9 microns and wavelengths shorter than 1.4 micron; infrared radiation emitted at these wavebands by a remote target undergoes minimum attenuation due to atmospheric absorption, scattering and particles prior to reception by a FLIR. A FLIR collects and collimates infrared radiation emitted by a remote target and passes it to infrared detectors which convert the infrared radiation into electrical signals which are amplified and processed by electronic circuitry for real-time viewing on a cathode-ray tube (CRT) or storage on hard copy. Infrared imaging devices spectrally integrate infrared emissions over a broad waveband to form a thermogram which is a composite of all infrared radiation emitted by a remote target. These basic imaging devices do not have the sensitivity required to spectrally discriminate between chemical warfare nerve agent thermal clouds and interferents and/or naturally occuring objects in the naval environment.

SUMMARY OF THE INVENTION

The present invention surmounts the disadvantages and limitations of the prior art by means of a forward looking infrared thermal imager (FLIR) modified with a spectral filter wheel (SFW) The FLIR collects infrared radiation emitted by a thermal cloud suspected of containing chemical warfare nerve agents. The incident infrared radiation is horizontally and vertically scanned, selectively filtered by the SFW and focused on a vertical array of infrared radiation detectors. Irradiance modulations of the detected infrared radiation are converted by the detectors to voltage fluctuations; these voltage fluctuations are amplified to drive a vertical array of light-emitting diodes (LEDs). The LEDs are scanned to focus a visible image onto a vidicon. The vidicon image is then converted into a thermogram.

The SFW has four infrared radiation bandpass filters, each of which is sequentially positioned to filter the infrared radiation emitted by the suspect thermal cloud, so that four separate thermograms are generated. Filter 1 passes approximately all incident infrared radiation in the 8 to 14 micron atmospheric window. Filter 2 is spectrally optimized to minimize the FLIR response to chemical warfare nerve agent infrared radiation emissions with respect to the background. Filters 3 and 4 are spectrally optimized to maximize the response of the FLIR to the two major infrared radiation emission bands characteristic of chemical warfare nerve agents. A comparison is then made among the the four thermograms as to variations in image contrast of the suspect thermal cloud with respect to its background to determine if the composition of the suspect thermal cloud includes chemical warfare nerve agents.

It is therefore a primary object of this invention to provide a modified infrared imaging apparatus and method for remotely detecting air-releases of chemical warfare nerve agents.

Another object of this invention is to provide a modified infrared imaging apparatus and method for passively detecting the infrared radiation emissions of chemical warfare nerve agents.

Yet another object of this invention is to provide an infrared imaging apparatus having a spectral filter wheel spectrally optimized to respond to infrared radiation wavebands characteristic of chemical warfare nerve agents.

A further object of this invention is to provide a spectral filter wheel capable of infrared radiation spectral discrimination between chemical warfare nerve agents and interferents and/or naturally occuring objects in the naval environment.

Other objects, advantages and novel features of the invention will become apparent from the following detailed description of the invention when considered in conjunction with the accompanying drawings wherein:

BRIEF DESCRIPTION OF THE DRAWINGS

FIG. 1 represents a schematic diagram of the preferred embodiment of the invention.

FIG. 2 is a plan view of the spectral filter wheel.

FIG. 3 is a graph of the infrared radiation emission bands characteristic of chemical warfare nerve agents.

FIG. 4 is a graph of the infrared radiation emissions of a gray body in the 8 to 14 micron atmospheric window.

FIG. 5a is a pictorial representation of a thermogram of a suspect thermal cloud generated by Filter 1.

FIG. 5b is a pictorial representation of a thermogram generated by Filter 2 when the suspect thermal cloud's composition is a chemical warfare nerve agent.

FIG. 5c is a pictorial representation of a thermogram generated by Filter 3 when the suspect thermal cloud's composition is a chemical warfare nerve agent.

FIG. 5d is a pictorial representation of a thermogram generated by Filter 4 when the suspect thermal cloud's composition is a chemical warfare nerve agent.

PREFERRED EMBODIMENT OF THE INVENTION

FIG. 1 represents a schematic diagram of a conventional forward looking infrared (FLIR) thermal imager, modified for the remote detection of chemical warfare nerve agents in an air-released suspect thermal cloud 10. An afocal system 14, in the preferred embodiment a Galilean telescope, collects the infrared radiation 12 emitted by the suspect thermal cloud 10. The collected infrared radiation 12 is reflected off a silver-backed scanning mirror 16 to a lens system 18; the scanning mirror 16 provides both horizontal sweep and vertical interlacing to give 320 lines of vertical resolution. This optical-mechanical scan mechanism permits the instantaneous field of view of the vertical detector array 24 to scan the spatial distribution of the collected infrared radiation 12 in the object plane. The lens system 18 focuses the reflected infrared radiation as it passes through the spectral filter wheel 20. The spectral filter wheel 20 is mechanically rotated to pass infrared radiation in selected passbands, these passbands being selected according to the infrared radiation emissivity characteristics of chemical warfare nerve agents in the 8 to 14 micron atmospheric window. The lens system 18 is designed such that the image plane of the filtered infrared radiation 22 lies on the surface of the vertical detector array 24. The vertical detector array 24 is composed of 160 mercury-cadmium-telluride photon detectors; in the alternative, the photon detectors could be fabricated from other materials, such as mercury-doped germanium, which have a useful infrared radiation detection range from 8 to 12 microns. Any of the known closed-cycle refrigerators, such as the Stirling refrigerator, a Joule-Thompson refrigerator, or a Claude refrigerator, may be used as a cooling means 26 to maintain the detector array 24 at the design operating temperature. The image plane irradiance modulations caused by horizontal scanning are converted by the vertical detector array 24 to voltage fluctuations 28. The voltage fluctuations 28 are amplified by 160 sets of preamplifiers 30; the amplified voltages 32 from the preamplifiers 30 drive light-emitting diodes (LEDs) 34, each amplifier driving a single LED. The LEDs 34 are arrayed in a form identical to that of the vertical detector array 24; this has the effect of converting the 8 to 12 micron infrared radiation fluctuations into modulations in the visible spectrum. A scanning mechanism 36 sweeps the LEDs 34 to focus a visible image 38 onto a vidicon 40. The vidicon signal 42 is then converted into a thermogram 44 which is displayed in real-time on a cathode-ray tube 46. Thermal imaging devices, sans spectral filter wheel 20, as used in the present invention are known in the prior art and their fabrication, operating parameters and characteristics are well known to those skilled in the art of thermal imaging; a representative example is Texas Instruments Model AN/AAS-28.

The spectral filter wheel 20 is schematically illustrated in FIG. 2 to show the face view of the preferred embodiment. The spectral filter wheel 20 is essentially separated into quadrants, each quadrant containing a spectral filter element having an infrared radiation passband transparent to a specific wavelength band of infrared energy emitted by the suspect thermal cloud 10. The detection of chemical warfare nerve agents in a suspect thermal cloud 10 with a FLIR modified with a spectral filter wheel 20 is dependent upon the image contrast of the generated thermogram 44, i.e., the discernible difference in the shades of gray between the suspect thermal cloud 10 and its background. The image contrast of the thermogram 44 is a function of several variables:

$$\text{Detection Contrast} = f\{\Delta T', \int R_\lambda \, d\lambda, C, L, a_\lambda\}$$

where $\Delta T'$ is the apparent temperature between the suspect thermal cloud 10 and its background, $\int R_{80} \, d\lambda$ is the integrated spectral response of the FLIR, C is the concentration of the chemical warfare nerve agents in the suspect thermal cloud 10, L is the optical path through the suspect thermal cloud 10 and $a_\lambda$ is the spectral absorption coefficient. An interferometric spectrometer was used to obtain the absolute spectral signatures of simulants, i.e., compounds whose infrared radiation emissivity signatures are substantially equivalent to chemical warfare nerve agents, and interferents air-released in varying naval environments. This device provided the absolute radiometric spectral signatures of the simulants and interferents and their backgrounds; it also provided the difference between these two values, the apparent temperature, which is the signal to which a FLIR responds. A computer optimization program was developed which specified spectral filters that maximized or minimized the ratio of simulant and interferent apparent temperatures with respect to specific naval backgrounds. This computer optimization program is described by S. R. Horman and W. J. Taczak in "OPTRAN: A Computer Code for Optimization of Electro-Optical Sensor Spectral Response," Naval Surface Weapons Center/Dahlgren Laboratory Technical Report 3909, 1978. This computer optimization model not only generated chemical warfare nerve agent spectral signatures, but also calculated background, atmospheric transmission and atmospheric emission effects. This computer program was used to generate performance specifications for the spectral filter wheel 20 bandpass interference filters. Spectral interference filter 48 is comprised of a germanium substrate with multi-layered interference coats such that it has an infrared radiation passband that extends from approximately 8.0 microns to approximately 12.0 microns. Spectral interference filter 48 is spectrally optimized to pass approximately all infrared radiation emitted by a gray body in the 8 to 14 micron atmospheric window. Spectral interference filter 50 is comprised of a germanium substrate with multi-layered interference coats such that it has an infrared radiation passband that extends from approximately 10.25 microns to approximately 10.75 microns. Spectral interference filter 50 is optimized to pass a wavelength band characteristic of chemical warfare nerve agents that has a relatively low infrared radiation emissivity; for gray bodies this wavelength passband has a relatively high infrared radiation emissivity. Spectral interference filter 52 is comprised of a germanium substrate with multi-layered interference coats such that it has an infrared radiation passband from approximately 9.60 microns to approximately 10.0 microns. Spectral interference filter 52 is spectrally optimized to a first major infrared radiation emission waveband characteristic of chemical warfare nerve agents and which is characterized by relatively high infrared radiation emissivity. Spectral interference filter 54 is comprised of a germanium substrate with multi-layered interference coats such that it has an infrared radiation passband from approximately 10.7 microns to approximately 12.0 microns. Spectral interference filter 54 is spectrally optimized to a second major infrared radiation emission waveband characteristic of chemical warfare nerve agents and which is characterized by relatively high infrared radiation emissivity.

In operation, the FLIR imager is orientated so that the suspect thermal cloud 10 is within the field-of-view of the imager. The suspect thermal cloud 10 is generated by the air-release of a gaseous composition by means of an aircraft or an exploding projectile. Incident infrared radiation 12 from the suspect thermal cloud 10 is collected by the afocal system 14. The scanning mirror 16 and the lens system 18 transmit the infrared radiation 12 to the spectral filter wheel 20. The spectral filter wheel 20 is initially configured so that spectral interference filter 48 is in the path of the infrared radiation 12. The filtered infrared radiation 22 in the 8 to 12 micron waveband is detected by the vertical detector array 24 which converts irradiance modulations to voltage fluctuations 28, the voltage fluctuations 28 are amplified to drive LEDs 34, the visible image 38 of the LEDs 34 is focused onto a vidicon 40 and the vidicon signal 42 is converted into a thermogram 44 which is displayed on the CRT 46. With spectral interference filter 48 aligned in the path of the incident infrared radiation 12, a thermogram 44 of the suspect thermal cloud 10, $T_1$, having an image contrast with respect to its background of $IC_1$, is generated (FIG. 5a). The infrared radiation 12 emitted by the suspect thermal cloud 10 is sequentially interrogated by means of spectral interference filters 50, 52, and 54, by rotation of the spectral filter wheel 20 to generate thermograms 44 of the suspect thermal cloud 10, $T_2$, $T_3$, and $T_4$, having image contrasts with respect to their backgrounds of $IC_2$, $IC_3$, and $IC_4$, respectively (FIGS. 5b, 5c, and 5d). A comparative analyses of the relative image contrasts among the four thermograms will determine whether the air-released suspect thermal cloud 10 is composed of chemical warfare nerve agent constituents.

Whether the suspect thermal cloud 10 is composed of chemical warfare nerve agents, or interferents, the relative image contrast $IC_1$ of thermogram $T_1$ will be higher than the image contrasts $IC_2$, $IC_3$ and $IC_4$, of thermograms $T_2$, $T_3$ and $T_4$. The passband of spectral interference filter 48 corresponds approximately to the 8 to 12 micron atmospheric window; the spatial distribution of the infrared radiation emissivity of the suspect thermal cloud 10 (FIGS. 3 or 4) will generate strong signals at all passband wavelengths so that thermogram $T_1$ will have a high image contrast, $IC_1$, with respect to its background. With spectral interference filter 50 in the infrared radiation pathway of the FLIR, a thermogram $T_2$, with a relatively weak image contrast with respect to its background, $IC_2$, will be generated if the suspect thermal cloud 10 is composed of chemical warfare nerve agent constituents. This result is reached, because as shown in FIG. 3, chemical warfare nerve agents have a relatively weak infrared radiation emissivity in this passband. By contrast, if the composition of the suspect thermal cloud 10 is an interferent, a thermogram $T_2$ with a relatively strong image contrast with respect to its background, $IC_2$, will be generated because of the relatively strong infrared radiation emissivity of an interferent in this passband (FIG. 4). With either spectral interference filters 52 or 54 in the infrared radiation pathway of the FLIR, thermograms $T_3$ and $T_4$ with relatively strong image contrasts with respect to their background, $IC_3$ and $IC_4$ respectively, will be generated. As seen in FIGS. 3 and 4 the infrared radiation emissivity of either an interferent or a chemical warfare nerve agent is relatively high at either of these passbands. Therefore, if the relative image contrasts with respect to the background, $IC_1$, $IC_2$, $IC_3$ and $IC_4$, of thermograms $T_1$, $T_2$, $T_3$ and $T_4$, respectively, are approximately equal, the composition of the suspect thermal cloud 10 is an interferent. If the suspect thermal cloud 10 is composed of chemical warfare nerve agents, the relative image contrasts with respect to the background, $IC_1$, $IC_3$ and $IC_4$ of thermograms $T_1$, $T_3$ and $T_4$, respectively, will be approximately equal; the relative image contrast with respect to the background, $IC_2$ of thermogram $T_2$, however, will be much weaker than $IC_1$, $IC_3$ or $IC_4$.

What is claimed and desired to be secured by United States Letters Patent is:

1. An apparatus for remotely detecting the presence of chemical warfare nerve agents in an air-released thermal cloud, comprising:
   - means for collecting incident infrared radiation emitted by said air-released thermal cloud;
   - means for focusing the collected infrared radiation;
   - means for selectively filtering the focused infrared radiation;
   - means for detecting the selectively filtered infrared radiation;
   - means for converting the detected infrared radiation into a plurality of thermograms; and
   - means for comparatively analyzing the image contrasts among said plurality of thermograms,
   - whereby comparative analyses of the variations in image contrasts among said plurality of thermograms generated by selectively filtering the infrared radiation emitted by said thermal cloud indicates the presence or absence of chemical warfare nerve agents in said thermal cloud 2. The invention as defined in claim 1 wherein:
   - said selectively filtering means comprises a spectral filter wheel interposed between said focusing means and said detection means;
   - said spectral filter wheel including
     - a first spectral interference filter spectrally optimized to maximize the response of said apparatus to infrared radiation emission wavelength bands from approximately 8 microns to approximately 14 microns;
     - a second spectral interference filter spectrally optimized to minimize the response of said apparatus to infrared radiation emission wavelength bands characteristic of chemical warfare nerve agents with respect to background infrared radiation;
     - a third spectral interference filter spectrally optimized to maximize the response of said apparatus to a first major infrared radiation emission wavelength band characteristic of chemical warfare nerve agents; and
     - a fourth spectral interference filter spectrally optimized to maximize the response of said apparatus to a second major infrared radiation emission wavelength band characteristic of chemical warfare nerve agents.

3. The invention as defined in claim 2 wherein:
   - said second spectral interference filter is spectrally optimized to pass infrared radiation having wavelengths from approximately 10.25 microns to approximately 10.75 microns.

4. The invention as defined in claim 2 wherein:
   - said third spectral interference filter is spectrally optimized to pass infrared radiation having wavelengths from approximately 9.60 microns to approximately 10.0 microns.

5. The invention as defined in claim 2 wherein:
   - said fourth spectral interference filter is spectrally optimized to pass infrared radiation having wavelengths from approximately 10.7 microns to approximately 12.0 microns.

6. A method for remotely detecting the presence of chemical warfare nerve agents in an air-released thermal cloud, comprising the steps of:
- aligning said thermal cloud within the field-of-view of an apparatus for remotely detecting the presence of chemical warfare nerve agents;
- collecting incident infrared radiation emitted by said thermal cloud;
- focusing the collected infrared radiation;
- selectively filtering the focused infrared radiation;
- detecting the selectively filtered infrared radiation;
- converting the detected infrared radiation into a plurality of thermograms; and
- comparatively analyzing the image contrast among said plurality of thermograms,
- whereby comparative analyses of the variations in image contrasts among said plurality of thermograms generated by sequentially filtering the infrared radiation emitted by said thermal cloud indicates the presence or absence of chemical warfare nerve agents in said thermal cloud.

7. A method as described in claim 6 wherein the selective filtering of the focused infrared radiation further comprises the steps of:
- passing the focused infrared radiation through a first spectral interference filter, said first spectral interference filter being spectrally optimized to infrared radiation emission wavelength bands from approximately 8 microns to approximately 14 microns, to subsequently generate a first thermogram;
- passing the focused infrared radiation through a second spectral interference filter, said second spectral interference filter being spectrally optimized to minimize the response of said apparatus to infrared radiation emission wavelength bands characteristic of chemical warfare nerve agents with respect to background infrared radiation, to subsequently generate a second thermogram;
- passing the focused infrared radiation through a third spectral interference filter, said third spectral interference filter being spectrally optimized to maximize the response of said apparatus to a first major infrared radiation emission wavelength band characteristic of chemical warfare nerve agents, to subsequently generate a third thermogram; and
- passing the focused infrared radiation through a fourth spectral interference filter, said fourth spectral interference filter being spectrally optimized to maximize the response of said apparatus to a second major infrared radiation emission wavelength band characteristic of chemical warfare nerve agents, to subsequently generate a fourth thermogram.

8. A method as described in claim 7 wherein:
said second spectral interference filter is spectrally optimized to pass infrared radiation having wavelengths from approximately 10.25 microns to approximately 10.75 microns.

9. A method as described in claim 7 wherein:
said third spectral interference filter is spectrally optimized to pass infrared radiation having wavelengths from approximately 9.60 microns to approximately 10.0 microns.

10. A method as described in claim 7 wherein:
said fourth spectral interference filter is spectrally optimized to pass infrared radiation having wavelengths from approximately 10.7 microns to approximately 12.0 microns.

11. In combination with a thermal viewer with an objective lens and a far infrared detector sensitive to a broad band of infrared frequencies, a subsystem for distinguishing one cloud of a first gaseous compound from an alternative cloud formed from a second gaseous compound when backlighted by a substantially uniform spectral distribution of light in the far infrared, comprising:
- a filter wheel mounted in said viewer between said objective lens and said detector having at least three apertures therein;
- one of said apertures being arranged to pass all far infrared frequencies in said broad band;
- each remaining aperture containing a filter which transmits only one of a group of different narrow bands of frequencies; and
- means mounted on said viewer to move said filter wheel so that said apertures are sequentially centered on the optical axis of said lens.

12. An apparatus according to claim 11 wherein said wheel contains 4 apertures.

13. An apparatus according to claim 11 wherein:
said filters consist of equal thickness plates of a material transparent to far infrared with at least one interference coating thereon.

* * * * *